United States Patent
Batzinger et al.

(10) Patent No.: US 6,888,347 B2
(45) Date of Patent: May 3, 2005

(54) OMNIDIRECTIONAL EDDY CURRENT PROBES, ARRAY PROBES, AND INSPECTION SYSTEMS

(75) Inventors: Thomas James Batzinger, Burnt Hills, NY (US); Shridhar Champaknath Nath, Niskayuna, NY (US); Curtis Wayne Rose, Mechanicville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/662,681

(22) Filed: Sep. 12, 2003

(65) Prior Publication Data

US 2005/0057247 A1 Mar. 17, 2005

(51) Int. Cl.$^7$ ................................................ G01N 27/82
(52) U.S. Cl. ........................ 324/242; 324/240; 324/243
(58) Field of Search ................................. 324/222, 228, 324/232, 234, 238–240, 242, 243, 244, 256–257, 260–262

(56) References Cited

U.S. PATENT DOCUMENTS

| | | |
|---|---|---|
| 3,876,932 A | 4/1975 | Domon et al. |
| 5,006,801 A | 4/1991 | Young |
| 5,182,513 A | 1/1993 | Young et al. |
| 5,262,722 A | 11/1993 | Hedengren et al. |
| 5,334,934 A | 8/1994 | Viertl |
| 5,345,514 A | 9/1994 | Mahdavieh et al. |
| 5,389,876 A | 2/1995 | Hedengren et al. |
| 5,418,547 A | 5/1995 | Mizukata et al. |
| 5,430,376 A | 7/1995 | Viertl |
| 5,442,286 A | 8/1995 | Sutton, Jr. et al. |
| 5,659,248 A | 8/1997 | Hedengren et al. |
| 5,903,147 A | 5/1999 | Granger, Jr. et al. |
| 6,175,234 B1 | 1/2001 | Granger, Jr. et al. |
| 6,414,483 B1 | 7/2002 | Nath et al. |
| 6,456,066 B1 * | 9/2002 | Burd et al. .................. 324/220 |

FOREIGN PATENT DOCUMENTS

| | | |
|---|---|---|
| EP | 0518635 A | 12/1992 |
| GB | 2109112 A | 5/1983 |

OTHER PUBLICATIONS

Patent Abstract of Japan, 2003240762A, H. Tatsuo, "Probe for Eddy Current Flaw Detection and Eddy Current Flaw Detecting Apparatus Using The Same", vol. 2003, No. 12, Aug. 27, 2003.

European Search Report, EP04255457, D. Joyce, Nov. 12, 2004.

* cited by examiner

*Primary Examiner*—Bot LeDynh
(74) *Attorney, Agent, or Firm*—Penny A. Clarke; Patrick K. Patnode

(57) ABSTRACT

An omnidirectional eddy current probe includes a number of sense coils arranged in a stack having a principal axis. At least two of the sense coils are rotationally skewed about the principal axis relative to one another. The sense coils are operatively connected to each other and a drive coil is also positioned in the stack. An impulse through the drive coil induces a magnetic influx through a conducting material specimen having a surface, thereby generating eddy currents on the surface. Secondary magnetic field generated from the eddy currents produces corresponding signals in the sense coils, and the signals are then analyzed for the possibility of surface flaw in the conducting material.

30 Claims, 6 Drawing Sheets

*Fig. 2*
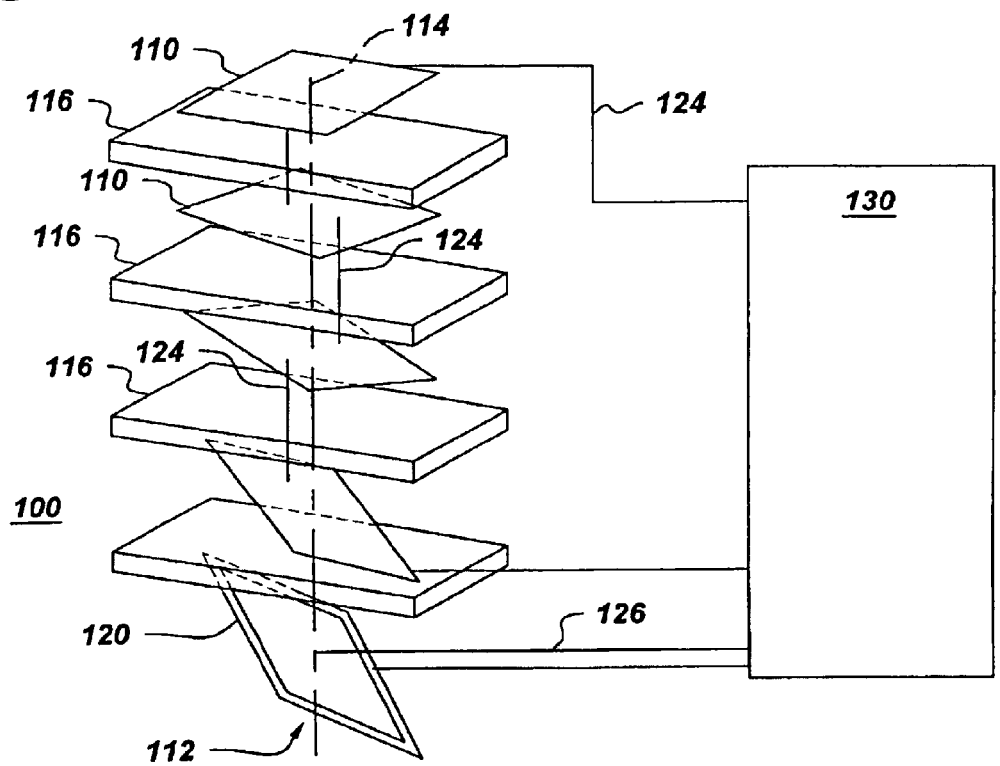
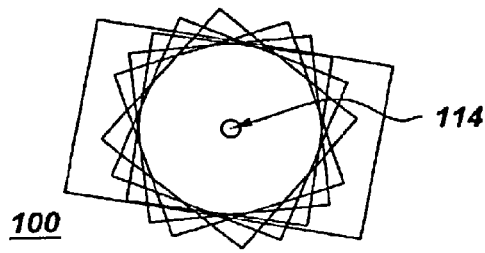
*Fig. 3*

US 6,888,347 B2

OMNIDIRECTIONAL EDDY CURRENT PROBES, ARRAY PROBES, AND INSPECTION SYSTEMS

BACKGROUND OF THE INVENTION

The present invention relates generally to eddy current inspection and, more specifically, to eddy current probes for non-destructive testing of conductive materials.

Eddy current inspection is a commonly used technique for non-destructive testing of conductive materials for surface flaws. Eddy current inspection is based on the principle of electromagnetic induction, wherein a drive coil carrying currents induces eddy currents within a test specimen, by virtue of generating a primary magnetic field. The eddy currents so induced in turn generate a secondary magnetic field, which induces a potential difference in the sense coils, thereby generating signals, which may be further analyzed for flaw detection. In case of a flaw in the test specimen, as for example, a crack or a discontinuity, the eddy current flow within the test specimen alters, thereby altering the signals induced in the sense coils. This deviation in the signals may be used to indicate the flaws.

Existing systems, such as those described in commonly assigned U.S. Pat. No. 5,389,876, Hedengren et al, "Flexible Eddy Current Surface Measurement Array for Detecting Near Surface Flaws in a Conductive Part," function on the above-mentioned principle. However, because magnetic fields are directional in nature, the eddy current probes described above are limited in their utility by the fact that a prior knowledge of crack orientation is required. This is also referred to as the directionality of eddy current probes.

Compensation for the directionality of conventional eddy current probes has been performed previously by repeatedly scanning a test specimen, with the eddy current probes being rotated slightly between each scan, in order to inspect the specimen for flaws along a number of orientations. However, this process is laborious and time consuming. Another possible approach would be to use an array probe designed to include number of elements formed on a substrate and slightly rotated. However, the latter arrangement would be inconvenient, in that it would either require a great deal of equipment or allow for a smaller scan.

Accordingly, there exists a need for an improved eddy current probe, array probe, and inspection system that overcomes the abovementioned problems inherent to compensating for the directionality of conventional eddy current probes.

BRIEF DESCRIPTION OF THE INVENTION

An omnidirectional eddy current probe includes a number of sense coils arranged in a stack having a principal axis. At least two of the sense coils are rotationally skewed about the principal axis relative to one another. The sense coils are operatively connected to each other, and a drive coil is also positioned in the stack.

Operationally, an impulse through the drive coil induces a magnetic influx through a conducting material specimen having a surface, thereby generating eddy currents on the surface. Secondary magnetic field generated from the eddy currents produces corresponding signals in the sense coils, and the signals are then analyzed for the possibility of surface flaw in the conducting material.

According to another embodiment of the present invention, an array of stacks as described above, forms a probe.

According to another embodiment of the invention, an omnidirectional eddy current inspection system includes an eddy current probe. The eddy current probe has a number of sense coils arranged in a stack, which has a principal axis. At least two of the sense coils are rotationally skewed about the principal axis relative to one another. A drive coil is positioned in the stack, and a number of electrical connections connect the sense coils. The inspection system also includes an eddy current instrument connected to the probe.

According to yet another embodiment of the invention, an omnidirectional eddy current array probe inspection system includes an eddy current array probe. The eddy current array probe includes multiple sense coils arranged in a number of stacks, and each of the stacks has a principal axis. At least two of the sense coils in a respective one of the stacks are rotationally skewed, relative to one another, about the respective principal axis. The eddy current probe also includes a number of drive coils, and each of the drive coils is positioned in a respective one of the stacks. The eddy current probe also includes a number of electrical connections, which connect the sense coils. The eddy current system also includes an eddy current instrument connected to the eddy current probe.

BRIEF DESCRIPTION OF THE DRAWINGS

The foregoing and other advantages and features of the invention will become apparent upon reading the following detailed description and upon reference to the drawings in which:

FIG. 2 is a perspective, blown-up view of an omnidirectional eddy current probe having a single eddy current stack;

FIG. 3 is a top view of the single eddy current stack of FIG. 2;

DETAILED DESCRIPTION OF SPECIFIC EMBODIMENTS

Figure 1:
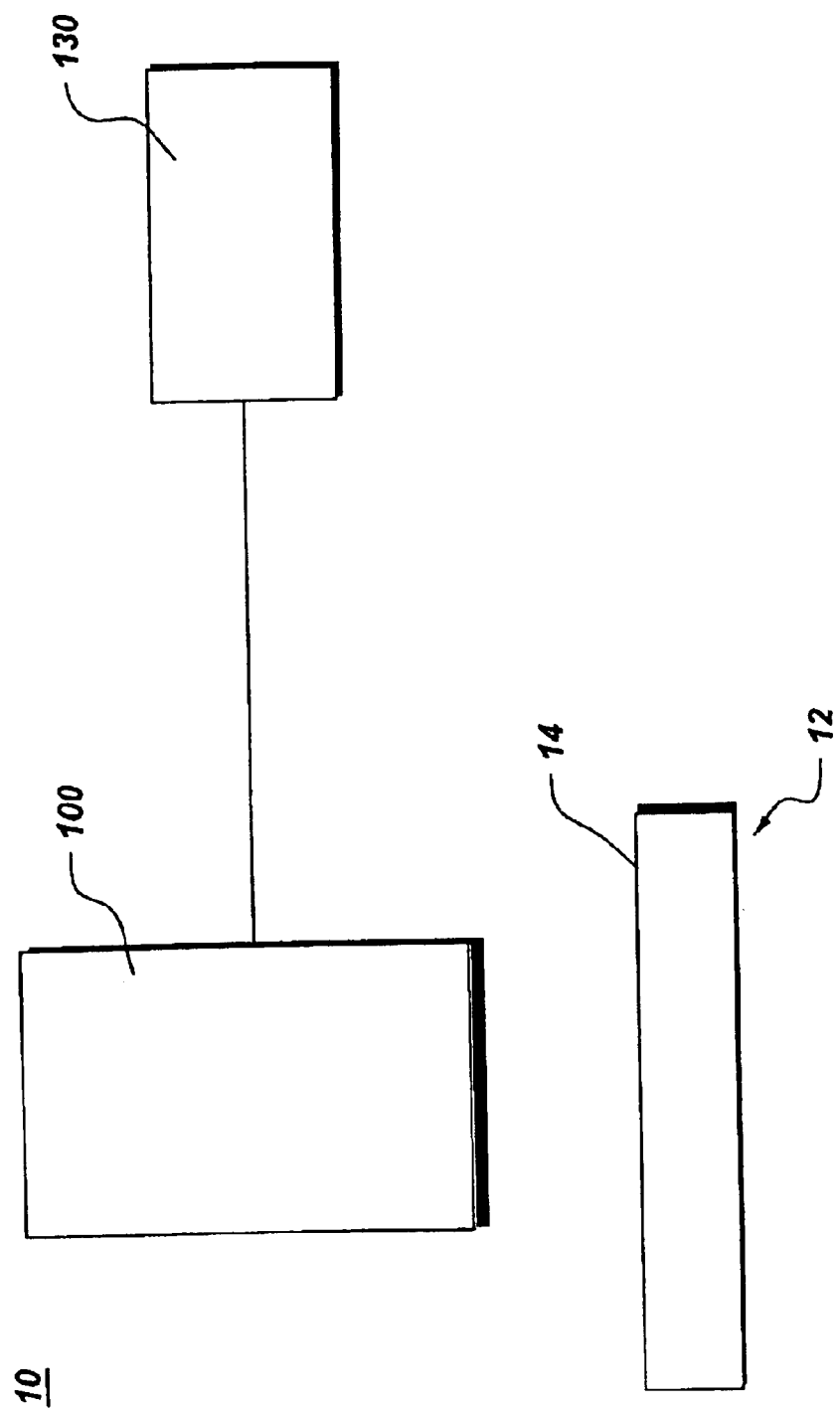
FIG. 1 illustrates an omnidirectional eddy current inspection system embodiment of the invention.

FIG. 1 shows an omnidirectional eddy current inspection system 10 including an omnidirectional eddy current probe 100 in communication with an eddy current instrument 130, in accordance with an embodiment of the present invention. The omnidirectional eddy current array probe 100 is positioned over an object to be inspected 12 having a surface 14. Exemplary test objects 12 include conductive materials.

Referring now to FIGS. 2 and 3, an omnidirectional eddy current probe 100 is shown. A number of sense coils (or sense coil elements) 110 are positioned on top of each other and centered about a straight line, which is called the principal axis 114, to form a stack 112. At least two of the sense coils 110 in the stack 112 are rotated with respect to each other, resulting in a rotationally skewed arrangement of the sense coils 110 within the stack 112, as illustrated by FIG. 3. It is noted here that an arrangement in which a group of consecutive sense coils are not rotationally skewed with respect to each other, but at least one of the sense coils external to the group is skewed with respect to that group, lies within the scope of the present invention. A (meaning at least one) drive coil 120 is positioned in the stack 112. More particularly, the drive coil 120 is disposed about the principal axis 114. According to a particular embodiment, the sense coils 110 are interconnected using electrical connections (or circuitry) 124 and are further connected to an eddy current instrument (ECI) 130. For this embodiment, the drive coil 120 is also connected by circuitry 126 to the eddy current instrument 130, which monitors the sense coils 110 and drives the drive coils 120. Eddy current instruments are known and, hence, will not be discussed in detail. It should be appreciated that the coils 110 and 120, and circuitry 124 and 126 shown in the figure are merely representational, and do not attempt to depict accurately, the coil shapes or electrical connections formed by the circuitry.

Operationally, the eddy current instrument 130 generates a current in the drive coil 120, which generates a magnetic flux. The magnetic field influx into the conducting material 12 generates eddy currents on the surface 14, which in turn generate a secondary magnetic field. In case of a surface flaw (not shown), the secondary magnetic field generated is deviant from its normal orientation when no flaw is present, to a direction corresponding to the flaw orientation. This deviant secondary magnetic field induces corresponding signals in the sense coils 110 thereby indicating the presence of the surface flaw. A potential difference induced in each sense coil 110 is added up by the virtue of interconnecting circuitry 124, and thereafter sensed by the eddy current instrument 130. Due to the rotational skewing, the sense coils 110 advantageously detect the directional deviation in the secondary magnetic flux corresponding to any crack orientation, thereby imparting an omnidirectional sensitivity to the probe 100.

Insulating substrate layers 116, which may desirably be flexible substrates (also indicated by reference numeral 116), are positioned between the sense and/or drive coils 110, 120. An exemplary flexible material for such layers is polyimide, one example of which is Kapton™, a registered trademark of E.I. du Pont de Nemours and Company of Wilmington, Del. More particularly, the sense and/or drive coils 110, 120 are formed on the flexible substrate(s) 116. To fix the flexible substrates 116 relative to one another, the flexible substrates 116 are bonded to each other, for example by a flexible adhesive layer (not shown), or otherwise held together in a physically stable arrangement to form the coil stack 112.

Figure 5:
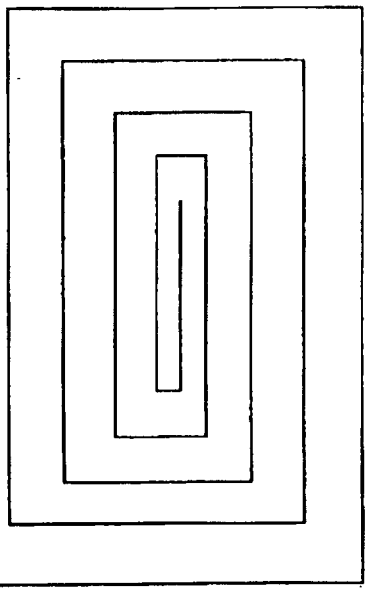
FIG. 5 depicts a rectangular eddy current coil.
Figure 4:
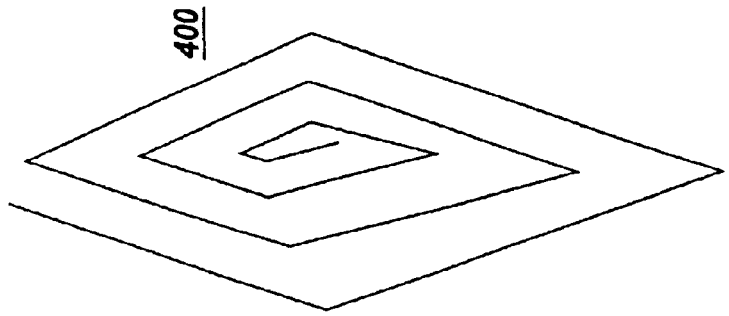
FIG. 4 illustrates a diamond shaped eddy current coil.

FIGS. 4 and 5 show a few exemplary shapes of sense coils 110 or drive coils 120, as for example, a diamond shaped coil 400 or rectangular coil 500. It may be further appreciated that the stack 112 may include sense coils 110 having an identical (common) geometry, as for example, diamond shaped coils. In an alternate embodiment, one or more of the sense coils 110 within the stack 112 may have a different geometry than do the other sense coils 110, for example, some sense coils 110 may be diamond shaped and some maybe rectangular.

Further, according to an embodiment of the present invention, the drive coil 120 may be one of the sense coils 110. For example, the drive coil 120 may be selected from the sense coils 110 based on the geometry of the sense coil 110, in order to generate a particular, desired magnetic field. Alternatively, the drive coil 120 may be distinct from the sense coils 110 as shown, for example, in FIG. 2.

Figure 6:
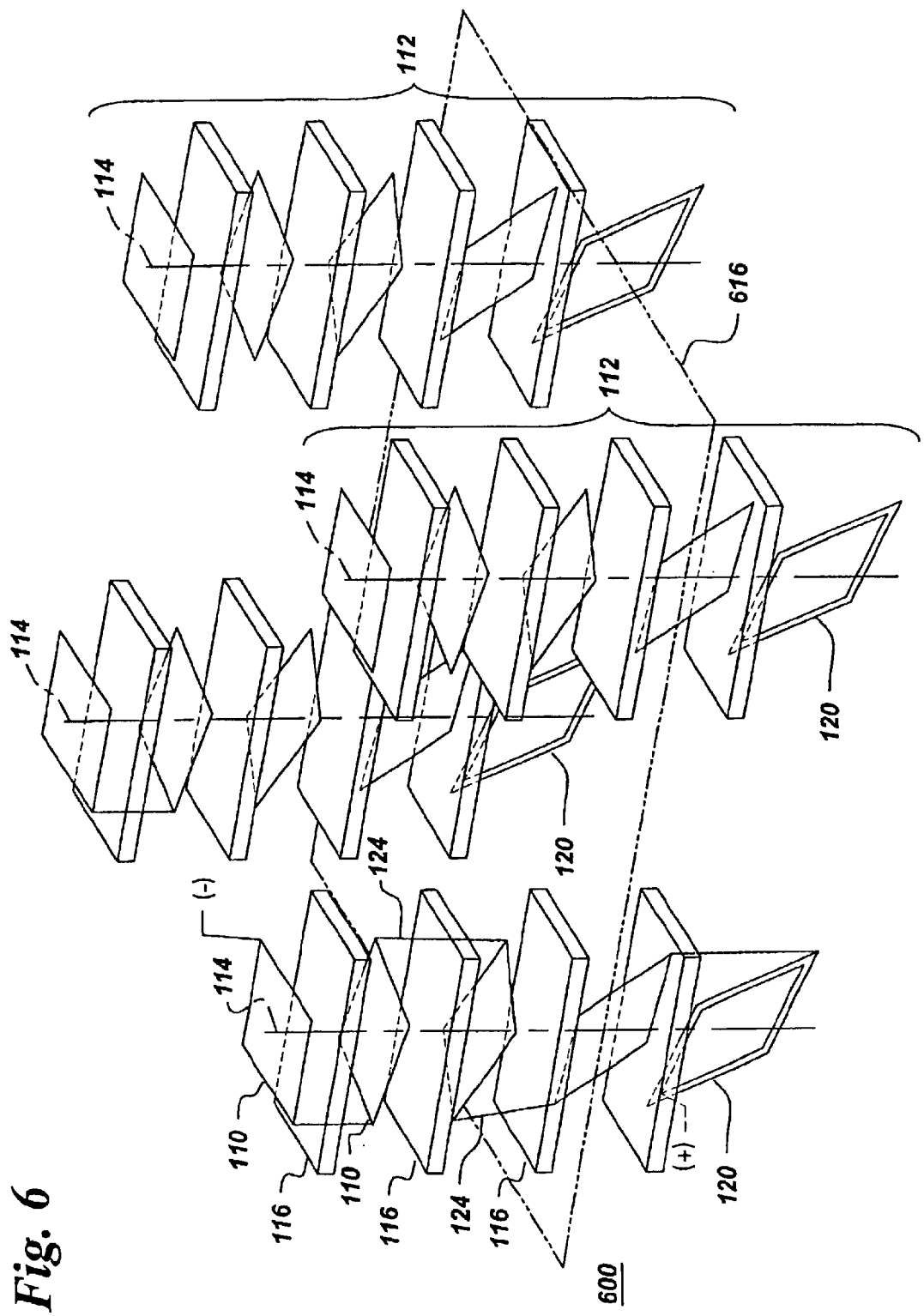
FIG. 6 is a perspective, blown-up view of an omnidirectional eddy current array probe embodiment that includes a number of eddy current stacks.
Figure 7:
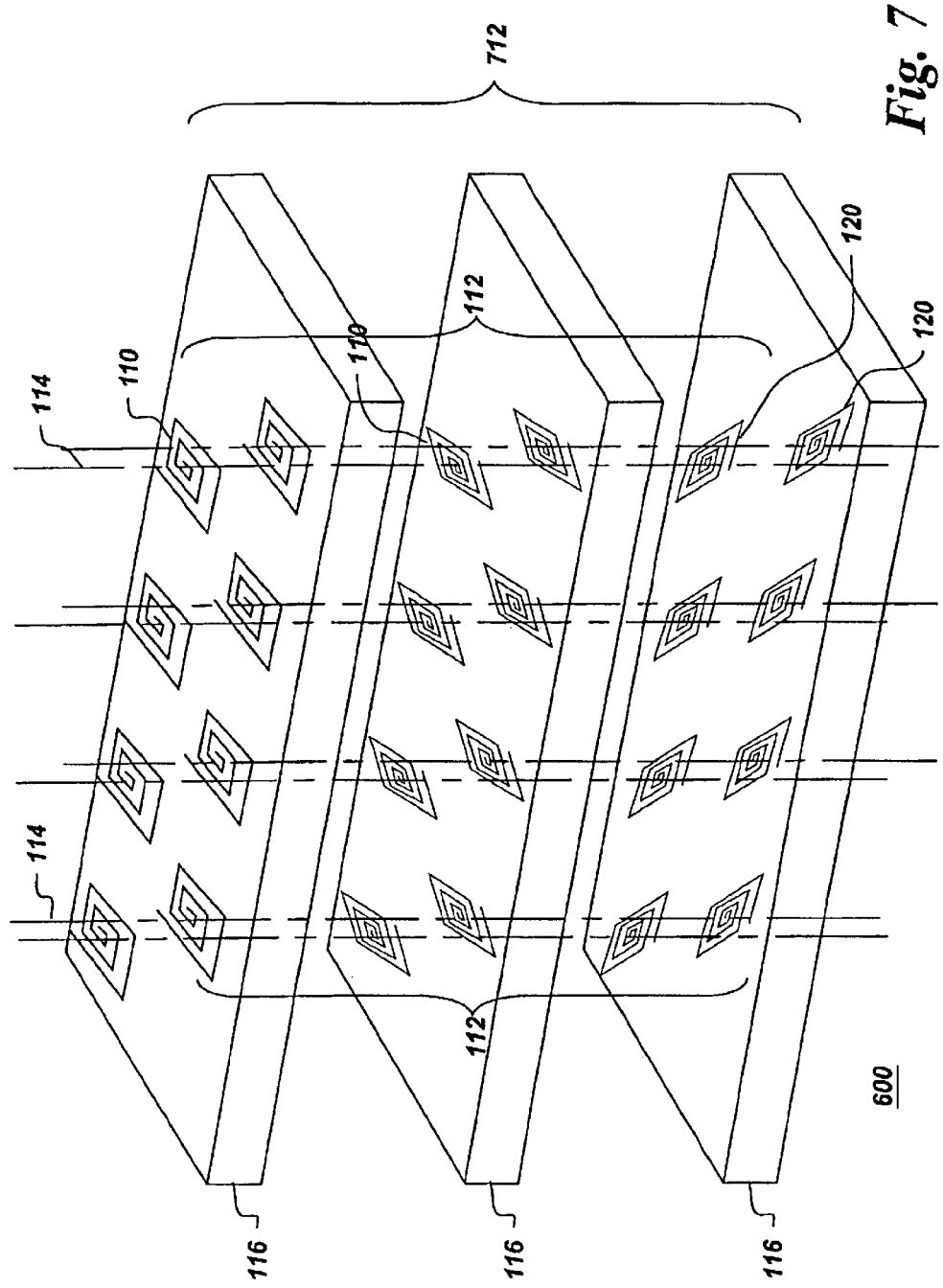
FIG. 7 is a perspective, blown-up view of another omnidirectional eddy current array probe embodiment.
Figure 8:
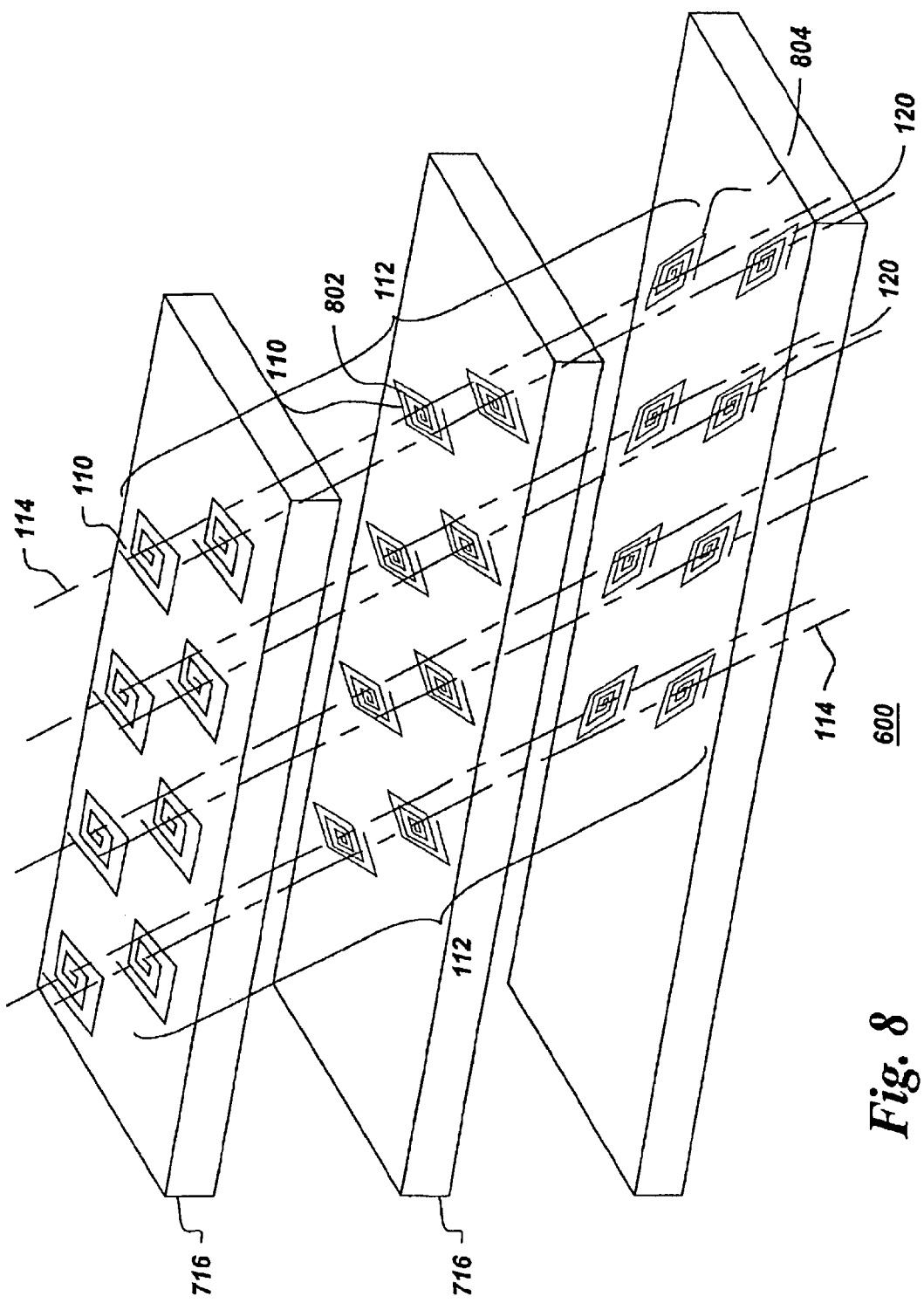
FIG. 8 is a perspective, blown-up view of another omnidirectional eddy current array probe, with a number of staggered layers.

In addition to an omnidirectional eddy current probe 100 comprising a single stack 112 of eddy current coils 110, 120, an omnidirectional eddy current array probe 600 is disclosed and illustrated in FIGS. 6–8. As shown, for example, in FIG. 6, a number of stacks 112 are arranged to form the omnidirectional eddy current array probe 600. The probe 600 may be connected to an eddy current instrument 130, as discussed above. The stacks 112 are described above with respect to FIGS. 2 and 3. A number of electrical connections 124 operatively connect the eddy current coils 110, 120 within the respective stacks 112. It is appreciated here that as shown in FIG. 6, the circuitry 124 is merely representative of the electric connections within a stack 112.

According to a particular embodiment, each of the stacks 112 in the probe 600 is similar, with the same number of sense coils 110 and a drive coil 120 in each of the stacks 112. More particularly, each of the coils 110 and 120 are placed at a corresponding positional order (level) in a stack 112. According to a more particular embodiment, each of the coils 110, 120 has the same geometry as a respective coil at the same level in another stack 112. The probe 600 illustrated in FIG. 6 also includes a number of substrates 116, each of the substrates 116 being positioned between at least one pair of sense coils 110. As noted above, the substrates 116 electrically insulate the pair of sense coils 110. For the exemplary embodiment of FIG. 7, a number of coils (sense 110 and drive 120) are formed on a single extended insulating substrate layer 116 which may be a flexible layer. As noted above, the extended layers 116 may be adhesively bonded to, or otherwise held in a physically stable arrangement over similar substrate layers to form a global stack 712. As used here, the term "global stack" refers to a stack of substrate layers 116. Because a number of coils (sense 110 and drive 120) are formed on each of the substrate layers, the global stack 712 encompasses a number of individual stacks 112, as shown in FIG. 7, for example. For the exemplary embodiment of FIG. 7, the substrates 116 are positioned on top of one another, such that the respective sense coils 110 and drive coil 120 are aligned along respective principal axes 114, as shown. As shown in FIG. 7, the sense coils 110 in each of the stacks 112 are rotationally skewed with respect to each other. Circuitry (not shown) interconnects the sense coils 110 within a stack 112. According to a particular embodiment, the circuitry further links array probe 600 to outside instrumentation, such as an eddy current instrument (not shown). Similarly, circuitry (not shown) connects the drive coils 120 of the stacks 112 to exterior instrumentation, such as an eddy current instrument. It will be appreciated that the coils 110, 120 may have identical or dissimilar geometries within a given stack 112 and further, that the coils 110 or 120 within a particular layer of the global stack 712 may also have identical or dissimilar geometries.

Another embodiment of the omnidirectional eddy current array probe 600 is illustrated in FIG. 8. As shown, the substrates 116, which are desirably flexible insulating layers, are staggered with respect to adjacent layers, so that the centers 802, 804 of the coils 110, 120 in adjacent layers are offset. Consequently, principal axes 114 of the coil stacks 112 are inclined with respect to the substrates 112. Such staggering of the layers advantageously affords a greater coverage to the probe 600.

It should be appreciated that in the embodiments illustrated by FIGS. 6–8, the omnidirectional eddy current array probe 600 may also include circuitry that connects sense coils 110 within a given level 616 or layers 716 across the coil stacks 112, in addition to connecting the coils 110 within a given coil stack 112. Similarly, the drive coils 120 may also be connected across the stacks 112. Additionally, for the embodiments illustrated in FIGS. 6–8, a coil stack 112 may have coils 110, 120 geometrically similar or dissimilar from the respective coils 110, 120 in other coil stacks 112 in the probe 600. It should also be appreciated that in this and related embodiments as illustrated by FIGS. 6, 7 and 8, the drive coil 120 of a particular stack 112 may be at positioned at a different layer than the drive coil 120 of another stack 112.

The abovementioned embodiments and equivalents thereof advantageously provide for an omnidirectional surface flaw detection system. Although the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An omnidirectional eddy current probe comprising:
   a plurality of sense coils arranged in a stack having a principal axis, wherein at least two of said sense coils are rotationally skewed about the principal axis relative to one another;
   electrical connections operatively connecting said sense coils; and
   a drive coil positioned in the stack.

2. The omnidirectional eddy current probe of claim 1, wherein said sense coils are electrically insulated from each other.

3. The omnidirectional eddy current probe of claim 2 further comprising at least one substrate positioned between a pair of said sense coils, said substrate electrically insulating the pair of said sense coils.

4. The omnidirectional eddy current probe of claim 3, wherein said at least one substrate is flexible.

5. The omnidirectional eddy current probe of claim 4, wherein at least one of said sense coils in the pair is formed on said at least one substrate.

6. The omnidirectional eddy current probe of claim 5, wherein two of said sense coils are formed on said at least one substrate.

7. The omnidirectional eddy current probe of claim 3, comprising a plurality of substrates, said substrates being stacked.

8. The omnidirectional eddy current probe of claim 7, wherein said substrates are bonded to maintain alignment of the stack.

9. The omnidirectional eddy current probe of claim 1, wherein at least two of said sense coils have a common geometry.

10. The omnidirectional eddy current probe of claim 1, wherein at least two of said sense coils have a different geometry.

11. The omnidirectional eddy current probe of claim 1, wherein said drive coil is one of said sense coils.

12. The omnidirectional eddy current probe of claim 1, wherein said drive coil (120) is not one of said sense coils.

13. An omnidirectional eddy current array probe comprising:
   a plurality of sense coils arranged in a plurality of stacks, each of the stacks having a principal axis, wherein at least two of said sense coils in the stack are rotationally skewed about the respective principal axis;
   a plurality of electrical connections operatively connecting said sense coils within the respective stacks; and
   a plurality of drive coils, each of said drive coils being positioned in a respective one of said stacks.

14. The omnidirectional eddy current array probe of claim 13 further comprising at least one substrate positioned between at least one pair of said sense coils in each of the stacks, said substrate electrically insulating said at least one pair of said sense coils.

15. The omnidirectional eddy current array probe of claim 14, wherein said at least one substrate is flexible.

16. The omnidirectional eddy current array probe of claim 14, comprising a plurality of substrates arranged in a global stack, each of said substrates being positioned between a respective pair of said sense coils in each of the stacks.

17. The omnidirectional eddy current array probe of claim 13, wherein at least two of said sense coils within a respective one of said stacks have a common geometry.

18. The omnidirectional eddy current array probe of claim 13, wherein at least two of said sense coils within a respective one of said stacks have a different geometry.

19. The omnidirectional eddy current array probe of claim 13, wherein at least two of said stacks have a common geometry.

20. The omnidirectional eddy current array probe of claim 13, wherein at least two of said stacks have a different geometry.

21. The omnidirectional eddy current array probe of claim 13, wherein a corresponding sense coil of each stack defines a level, and at least two of said sense coils in a respective one of the levels have a common geometry.

22. The omnidirectional eddy current array probe of claim 13, wherein none of said drive coils is one of said sense coils.

23. The omnidirectional eddy current array probe of claim 13, wherein at least one of said drive coils is one of said sense coils.

24. The omnidirectional eddy current array probe of claim 16, wherein a center of one of said sense coils is offset with respect to a center of another of said sense coils within the respective stack, resulting in a staggered arrangement of said sense coils.

25. An omnidirectional eddy current inspection system comprising:
   an eddy current probe comprising:
      a plurality of sense coils arranged in a stack having a principal axis, wherein at least two of said sense coils are rotationally skewed about the principal axis relative to one another,
      a drive coil positioned in the stack, and
      a plurality of electrical connections connecting said sense coils; and
   an eddy current instrument connected to said probe.

26. The omnidirectional eddy current inspection system of claim 25, wherein each of said sense coils is individually monitored by said eddy current instrument.

27. The omnidirectional eddy current inspection system of claim 25, wherein said sense coils are monitored simultaneously through a single channel by said eddy current instrument.

28. An omnidirectional eddy current inspection system comprising:

an eddy current array probe comprising:
- a plurality of sense coils arranged in a plurality of stacks, each of the stacks having a principal axis, wherein at least two of said sense coils in a respective one of the stacks are rotationally skewed about the respective principal axis,
- a plurality of drive coils, each of said drive coils being positioned in a respective one of the said stacks, and
- a plurality of electrical connections connecting said sense coils; and an eddy current instrument connected to said probe.

29. The omnidirectional eddy current inspection system of claim 28, wherein each of said sense coils in said probe is individually monitored by said eddy current instrument.

30. The omnidirectional eddy current inspection system of claim 28, wherein each of said sense coils within a respective one of said stacks is monitored simultaneously through a single channel by said eddy current instrument.

* * * * *